(12) United States Patent
Sharma et al.

(10) Patent No.: US 7,247,738 B2
(45) Date of Patent: Jul. 24, 2007

(54) METHOD OF PREPARATION OF ANTICANCER TAXANES USING 3-[(SUBSTITUTED-2-TRIALKYLSILYL) ETHOXYCARBONYL]-5-OXAZOLIDINE CARBOXYLIC ACIDS

(75) Inventors: Arun Prakash Sharma, West Bengal (IN); Subrata Sarkar, West Bengal (IN); Jyan Shankar Mahanty, West Bengal (IN)

(73) Assignee: Dabur India Limited, Nadia (IN)

( * ) Notice: Subject to any disclaimer, the term of this patent is extended or adjusted under 35 U.S.C. 154(b) by 84 days.

(21) Appl. No.: 10/430,433

(22) Filed: May 7, 2003

(65) Prior Publication Data

US 2003/0229135 A1 Dec. 11, 2003

(30) Foreign Application Priority Data

May 7, 2002 (IN) ....................................... 269/02

(51) Int. Cl.
*C07D 305/14* (2006.01)
(52) U.S. Cl. ........................................ 549/510; 549/511
(58) Field of Classification Search ................ 549/510, 549/511
See application file for complete search history.

(56) References Cited

U.S. PATENT DOCUMENTS

| | | | |
|---|---|---|---|
| 5,476,954 A | 12/1995 | Bourzat et al. | |
| 5,616,739 A | 4/1997 | Mas et al. | |
| 5,637,723 A | 6/1997 | Commercon et al. | |
| 6,002,022 A | 12/1999 | Authelin et al. | |
| 6,022,985 A | 2/2000 | Authelin et al. | |
| 6,197,980 B1 | 3/2001 | Durand et al. | |
| 6,506,905 B1 | 1/2003 | Prakash et al. | |

OTHER PUBLICATIONS

U.S. Appl. No. 10/431,499, filed Aug. 5, 2003, Sharma et al.
U.S. Appl. No. 10/430,433, filed May 7, 2003, Sharma et al.
U.S. Appl. No. 10/358,384, filed Feb. 5, 2003, Sharma et al.
U.S. Appl. No. 10/419,782, filed Apr. 22, 2003, Sharma et al.
U.S. Appl. No. 10/213,431, filed Aug. 7, 2002, Sharma et al.
Wani et al., J. Am. Chem. Soc., vol. 93, pp. 2325 and 2326, (1971).

*Primary Examiner*—Rita Desai
(74) *Attorney, Agent, or Firm*—Venable LLP; Marina V. Schneller

(57) ABSTRACT

This invention relates to a process for preparation of taxanes comprising
subjecting 7,10-diprotected intermediates 7-O-(2-haloacyl) baccatin III 6c or 7,10-O-di-(2-haloacyl)-10-deacetylbaccatin III 6b to a step of coupling with (4S,5R)-3-[(2-alkyl/aryl-2-trialkylsilyl)ethoxy-carbonyl]-4-aryl-2-substituted-1, 3-oxazolidine-5-carboxylic acid 1 in the presence of a condensation agent, an activating agent and an aromatic hydrocarbon to obtain 7-O-[2-(haloacyl)]-13-[(4S,5R)-4-aryl-2-substituted-3(2-unsubstituted/substituted-2-trialkylsilyl)-ethoxycarbonyl-1,3-oxazolidinyl-5-carbonyl]baccatin III 7a or 7,10-di-O[2-(haloacyl)]-13-[(4S,5R)-4-aryl-2-substituted-3-(2-unsubstituted/substituted-2-trialkylsilyl) ethoxy-carbonyl-1,3-oxazolidinyl-5-carbonyl]-10-deacetyl-baccatin III 7b;
treating the coupled products 7-O-[2-(haloacyl)]-13-[(4S, 5R)-4-aryl-2-substituted-3-(2-substituted-2-trialkylsilyl) ethoxy-carbonyl-1,3-oxazolidinyl-5-carbonyl]baccatin III 7a or 7,10-di-O-[2[(haloacyl)]-13-[(4S,5R)-4-aryl-2-substituted-3-(2-substituted-2-trialkylsilyl)ethoxycarbonyl-1,3-oxazolidinyl-5-carbonyl]-10-deacetylbaccatin III 7b with tetraalkylammonium halide in a haloalkane to obtain free amine of structure 8;
treating free amine 8 with acid chloride or acid anhydride in the presence of a base in a heterogeneous phase to obtain the intermediates of structure 9;
subjecting the intermediates of compound 9 to the deprotection of 2-haloacyl group under mild alkaline condition at −20 to +40° C. for 6–24 h in the presence of ammonia or aliphatic amines or aromatic amines or their combination to obtain paclitaxel or docetaxel.

9 Claims, No Drawings

METHOD OF PREPARATION OF ANTICANCER TAXANES USING 3-[(SUBSTITUTED-2-TRIALKYLSILYL) ETHOXYCARBONYL]-5-OXAZOLIDINE CARBOXYLIC ACIDS

The present invention relates to the process of manufacturing of anticancer taxanes such as paclitaxel, docetaxel and their structural analogs from their biogenetic precursor 10-DAB using a novel oxazolidine carboxylic acid side chain.

FIELD OF THE INVENTION

The present invention relates to a novel oxazolidine carboxylic acid and a process for its preparation. The invention further relates to a process for the preparation of paclitaxel, docetaxel and structural analogs using such oxazolidine carboxylic acid.

BACKGROUND OF THE INVENTION

Paclitaxel is a diterpene taxane found in very low concentration in the bark of Pacific yew tree *Taxus brevifolia*. Therefore, a number of semi-synthetic strategies have been developed for its synthesis from more readily available 10-DAB. However, the taxane nucleus is highly prone to degradation and semis-synthetic crude materials are often produced contaminated with structurally similar impurities, thereby necessitating elaborate purification procedure using HPLC. In view of the above facts it becomes highly desirable to develop alternative routes for synthesis of paclitaxel which involves minimal degradation along the synthetic pathway.

Any synthetic protocol for the semi-synthesis of paclitaxel/docetaxel generally consists of a) selective acylation/protection at similarly reactive C-7 and C-10 hydroxyl groups. Among the 1, 7, 10 and 13-hydroxyl groups in 10-DAB, the order of reactivity is 7>10>13>1. Therefore, selective esterification of 13-hydroxyl group requires prior protection of both 7 and 10-hydroxyl groups. Furthermore, if acetyl group is required in the final product, as in the case of paclitaxel, then 7-hydroxyl is to be protected first followed by acetylation of 10-hydroxyl. This requires selection of appropriate protecting groups, which can be put selectively and removed selectively under mild condition. Recently, we have explored the use of haloalkyl acid chlorides as protecting groups (U.S. Provisional patent Application 60/311,077). These haloalkonoyl groups undergo hydrolysis faster than unsubstituted alkonoyl groups and their deprotection causes minimum degradation. We have found that such haloalkyl acid chlorides specifically 2-haloalkyl acid chlorides can be used for selective protection in taxanes and can be selectively deprotected.

b) selective esterification of 13-hydroxyl group with a suitably protected N-benzoylphenylisoserine. It has been found that α-hydroxy-β-amidoaryl moiety at the 13-hyroxyl of the taxane moiety is essential for its anti-cancer activity (Wani et. al *J. Am. Chem. Soc.* 93, pp 2325, 1971). Esterification at 13-hydroxyl of taxane is very sluggish due its stereo-electronic disposition. It is known from literature that esterification step proceeds to completion with cyclic forms of α-hydroxy-β-amidoarylcarboxylic acids. Furthermore, when cyclic forms of C-13 side chain is used, no 2'-epimers is obtained as side product. Therefore, new cyclic forms of side chains, which undergo facile coupling with suitably protected 10-DAB in high yield under simple reaction condition without their use in large excess, are required for developing better and more efficient alternative routes for synthesis of paclitaxel and its analogs.

c) conversion of side chain precursor part into side chain and removal of the protecting groups from baccatin part. These reaction conditions should be mild in nature to afford final material in high yield with very few side products. For successful commercial production, it is desirable that the crude semi-synthetic taxane is produced with such purity that it could easily be purified into pharmaceutical grade material.

Most of the nitrogen protecting groups used so far in oxazolidine carboxylic acid require either harsh acidic condition or hydrogenolysis for their removal.

Thus, e.g. U.S. Pat. No. 5,476,954 to Bourzat et al describes an oxazolidine side chain having a tert-butoxy carbonyl protecting group on the nitrogen atom. After coupling with suitably protected 10-DAB, this protecting group is removed by treating the coupled product in 98% formic acid medium and removal of acid by evaporation to obtain an amine which is then converted into the corresponding benzoyl derivative. The harsh acidic condition reaction and evaporation decomposed the free amine and resulted in the final product with close taxane related impurities.

Also, Mas et al. in the U.S. Pat. No. 5,616,739 describes a process in which the coupled product, obtained from coupling of an oxazolidine sidechain having a 2-trichloroethoxy carbonyl group and a protected 10-DAB. The resulting coupled product undergo reductive cleavage by using Zn-acetic acid to achieve simultaneous removal of side chain protecting groups and 7/10-hydroxyl protecting group. The resultant amine is then suitably protected to obtain the taxane. The disadvantage of this process is the free amine obtained in the above process where the 7/10 position is open. The free amine degrade very fast when the protection of 7/10 position is open and a number of decomposition product are formed.

On the other hand, U.S. Pat. No. 5,637,723 issued to Rhone Poulenc Rorer S. A. in 1997 described an oxazolidine carboxylic acid, which incorporated benzoyl group as the nitrogen-protecting group. Consequently, the coupled product obtained from the oxazolidine carboxylic acid and protected 10-DAB, upon deprotection did not require to be protected by a benzoyl group. Again this procedure requires deprotection of the coupled product in an acidic medium and is applicable only to Paclitaxel since the benzoyl group is inactive and hard to remove.

With a view to develop side chain precursor which can be processed to paclitaxel/docetaxel after coupling with suitably protected taxane, under very mild acid and preferably neutral condition, the applicants have found the following oxazolidine carboxylic acid of general structure 1. It has a (2-trialkylsilyl)ethoxycarbonyl/(2-phenyl-2-trialkylsilyl) ethoxycarbonyl group as nitrogen protecting group, which can be cleaved under very mild condition, and therefore degradation of taxane nucleus

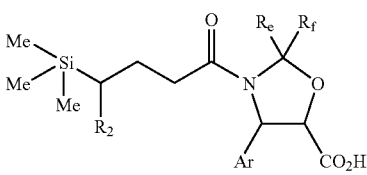

R₂=Hydrogen or phenyl can be avoided. The other N, O-bifunctional protecting group then undergoes cleavage very fast without degradation under mild condition.

(2-Trialkylsilyl)ethoxycarbonyl groups are more labile than t-butoxy carbonyl and 2-trichloroethoxy carbonyl nitrogen protecting group reported in prior art. In fact (2-phenyl-2-trialkylsilyl) ethoxycarbonyl group can be cleaved under almost neutral condition.

Therefore, these oxazolidine carboxylic acids have emerged as new type of side chain precursor for the synthesis of paclitaxel and docetaxel.

Herein the applicant have described new intermediates for taxoid anticancer drugs, their process of synthesis and process for synthesis of paclitaxel and similar analogs using them (Scheme-1).

OBJECTS OF THE INVENTION

The object of this invention is to propose a novel oxazolidine carboxylic acid.

Another object of this invention is to propose a novel process for the preparation of anticancer taxanes.

Another object of the present invention is to propose a new process for the preparation of intermediates of taxanes.

Yet another object of this invention is to propose a process for preparation of paclitaxel, docetaxel and their analogues using intermediates, which minimize degradation during the process and thereby increase the purity of the target product.

SUMMARY OF THE INVENTION

The present investigation relates to synthesis of novel taxane intermediates 7, 8 and 9 which can be easily be purified to pharmaceutical grade material.

The present invention consists of:

i) 5-oxazolidine carboxylic acid of general structure 1(a,b,c) undergo facile coupling with 7-O-(2-chloro acetyl)-baccatin III 6c in the presence of a condensation agent and an activating agent. The reaction can be carried out in an aromatic hydrocarbon, preferably toluene at temperature between 0° to 100° C. to obtain 7-O-(2-chloroacetyl)-13-[(4S,5R)-4-phenyl-2-substituted-3-(2-unsubstituted/substituted-2-trimethylsilyl)ethoxycarbonyl-1,3 oxazolidinyl-5-carbonyl]baccatin III 7a(from 6c+1a),7c(from 6c+1b), and 7e(from 6c+1c), On the other hand 7,10-O-di-(2-chloroacetyl)-10-deacetylbaccatin III 6b is coupled under similar reaction condition with 1(a,b,c) to obtain 7,10-O-di-[2-chloro acetyl]-13-[(4S,5R)-4-phenyl-2-substituted-3-(2-unsubstituted/substituted-2-trimethylsilyl)ethoxycarbonyl-1,3-oxazolidinyl-5-carbonyl]-10-deacetyl baccatin III 7b (from 6b+1a). 7d (from 6b+1b). and 7f (from 6b+1c).

In the general structure 1

$R_3$ and $R_4$ are independently selected from hydrogen, alkyl, alkenyl, alkynyl, aryl, heteroaryl, alkoxy, alkenyloxy, alkynyloxy, aryloxy, and heteroaryloxy. In the preferred structure, $R_4$ is hydrogen and $R_3$ is aryl, more preferably p-methoxyphenyl or both $R_3$ and $R_4$ are methyl.

$R_2$ is hydrogen or phenyl

In the general structure 7 legends are defined as stated above.

ii) opening of the oxazolidine ring in the coupled product 7 along with simultaneous deprotection of (2-substituted-2-trialkylsilyl)ethoxycarbonyl group can be effected by fluoride induced fragmentation leading to fewer side reactions. Among the sources of fluoride ion, tetrabutylammonium fluoride is preferable.

Alternatively, deprotection of (2-unsubstituted/substituted-2-trialkylsilyl)ethoxycarbonyl group can also be achieved under mild acidic condition.

iii) the resultant free amines 8 are converted into the corresponding amides by known literature procedure, which consist of treating the amines with acid chlorides or acid anhydrides in the presence of a base in a heterogeneous phase to obtain the intermediate 9.

iv) the intermediate 9, under mild alkaline condition at −20° to +40° C. for 6–24 h in the presence of ammonia or aliphatic amines or aromatic amines or their combination, undergoes selective deprotection of 2-chloroacetyl groups other acetyl remain intact without degradation to afford Paclitaxel or Docetaxel.

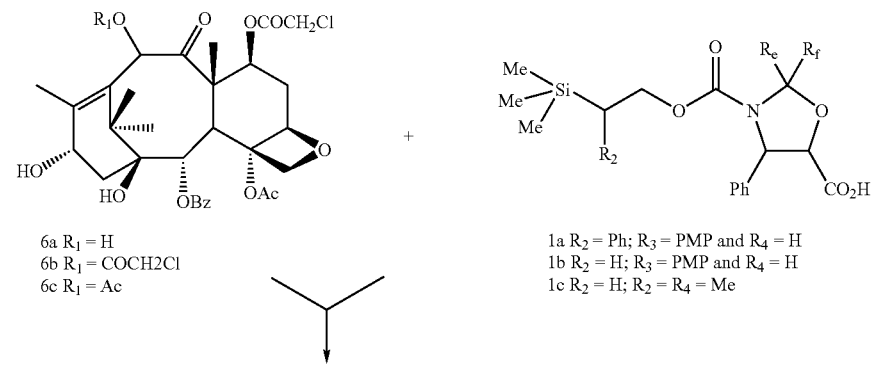

6a R₁ = H
6b R₁ = COCH2Cl
6c R₁ = Ac

1a R₂ = Ph; R₃ = PMP and R₄ = H
1b R₂ = H; R₃ = PMP and R₄ = H
1c R₂ = H; R₂ = R₄ = Me

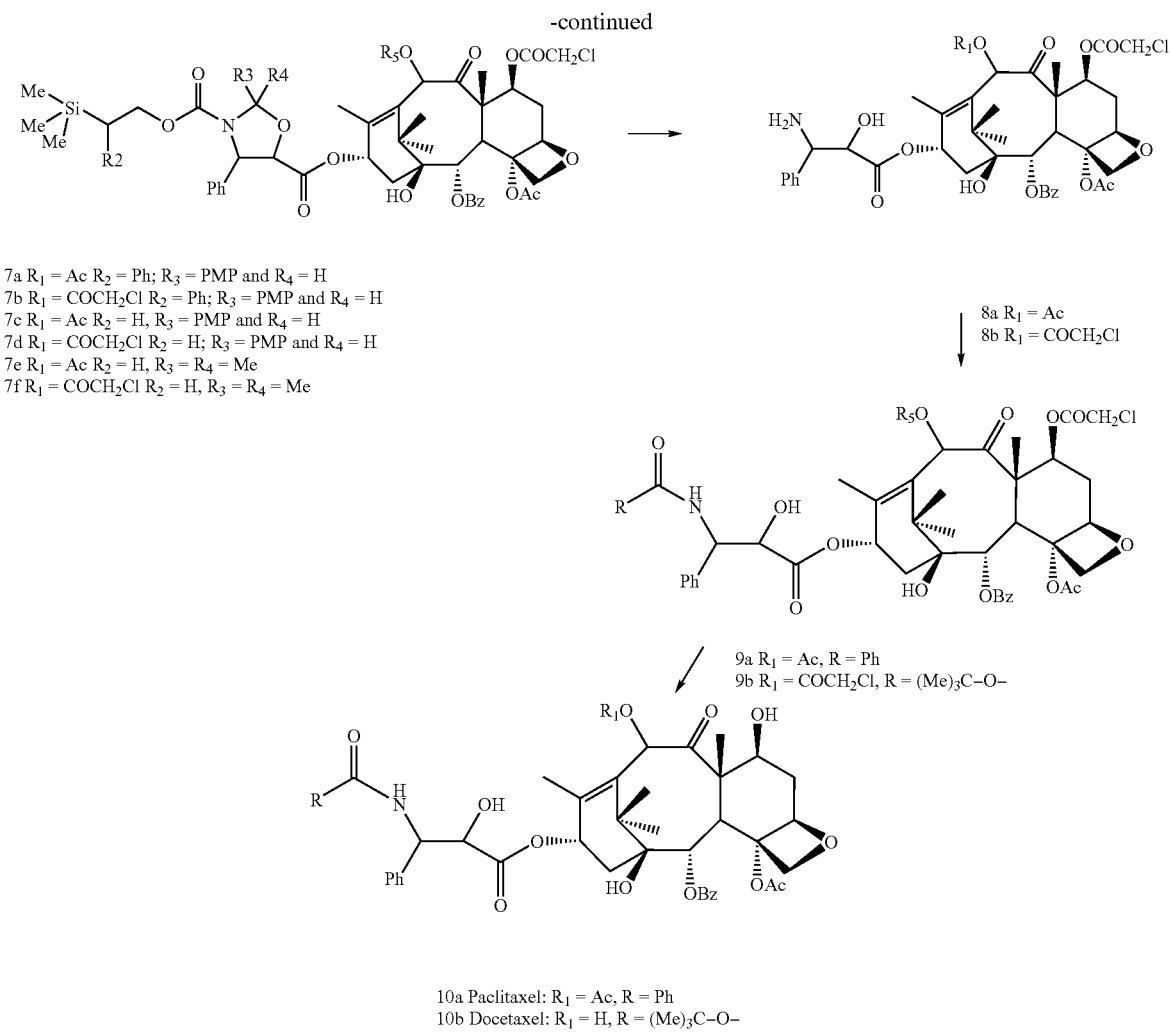

7a R₁ = Ac R₂ = Ph; R₃ = PMP and R₄ = H
7b R₁ = COCH₂Cl R₂ = Ph; R₃ = PMP and R₄ = H
7c R₁ = Ac R₂ = H, R₃ = PMP and R₄ = H
7d R₁ = COCH₂Cl R₂ = H; R₃ = PMP and R₄ = H
7e R₁ = Ac R₂ = H, R₃ = R₄ = Me
7f R₁ = COCH₂Cl R₂ = H, R₃ = R₄ = Me 8a R₁ = Ac
8b R₁ = COCH₂Cl 9a R₁ = Ac, R = Ph
9b R₁ = COCH₂Cl, R = (Me)₃C–O–

10a Paclitaxel: R₁ = Ac, R = Ph
10b Docetaxel: R₁ = H, R = (Me)₃C–O–

DETAILED DESCRIPTION OF THE INVENTION

The present invention provides a process for coupling of (4R,5S)-4-phenyl-2-substituted-3-[(2-substituted/unsubstituted-2-trialkylsilyl)ethoxycarbonyl]-1,3-oxazolidine-5-carboxylic acids 1 with protected 10-DAB 6. It also describes the conversion of the resultant coupled product 7 to paclitaxel or docetaxel via intermediates 8 and 9 and incorporates these intermediates.

(4R,5S)-4-phenyl-2-substituted-3-[(2-unsubstituted/substituted-2-trialkylsilyly)ethoxycarbonyl]-1,3-oxazolidine-5-carboxylic acids 1 are coupled with 7-O-(2-chloroacetyl) baccatin III 6c or 7,10-O-di-(2-chloroacetyl)-10-deacetylbaccatin III 6b in the presence of a condensation agent and an activating agent in an aromatic hydrocarbon as solvent to obtain 7-O-[2-chloroacetyl]-13-[(4S,5R)-4-phenyl-2-substituted-3-(2-unsubstituted/substituted-2-trialkylsilyl)ethoxycarbonyl-1,3-oxazolidinyl-5-carbonyl]baccatin III or 7,10-O-di-[2-chloroacetyl]-13-[(4S,5R)-4-phenyl-2-substituted-3-(2-unsubstituted/substituted-2-trialkylsilyl)ethoxycarbonyl-1,3-oxazolidinyl-5-carbonyl]-10-deacetyl baccatin III respectively. The reaction is carried out at temperature between 0–100° C., more preferably at 40–80° C., most preferably at 60° C. Among aromatic hydrocarbons, toluene is found most suitable. Opening of the oxazolidine ring in the coupled product 7 along with simultaneous deprotection of the nitrogen protecting (2-unsubstituted/substituted-2-trialkylsilyl)ethoxycarbonyl group was found to be structure dependent; the determining factor being the nitrogen-protecting group. In case of a (2-substituted-2-trialkylsilyl)ethoxycarbonyl group e.g. (2-phenyl-2-trimethylsilyl)ethoxycarbonyl group as the nitrogen protecting group in the coupled product, the desired deprotection could be achieved by fluoride induced fragmentation leading to fewer side reaction. Among the sources of fluoride ion, tetraalkylammonium fluoride is preferable. The reaction is carried out by treating the coupled product 7a or 7b with two equivalents of tetraalkylammonium fluoride, preferably tetrabutylammonium fluoride in a haloalkane, preferably dichloromethane for 15 min to 120 min, preferably 30 min at 0–40° C., preferably at 25° C. to obtain the corresponding free amine 8a.

Alternatively, deprotection of (2-trialkylsilyl)ethoxycarbonyl group e.g. (2-trimethylsilyl) ethoxycarbonyl group or (2-substituted-2-trialkylsilyl)ethoxycarbonyl group e.g. (2-phenyl-2-trimethylsilyl)ethoxycarbonyl group, the nitrogen protecting group in the coupled product 7 can be achieved by using acidic medium. Treating coupled product 7 with 60% aqueous trifluoroacetic acid (10 times) and then mixing at temperature between 18–25° C., preferably 22° C. for 3–6 h, preferably 4.5 hours effects deprotection along with desired opening of the oxazolidine ring. This is followed by decomposition of excess acid by disodiumhydrogen phosphate work-up to obtain free amines 8.

The yields obtained by using acidic medium to obtain free amines 8 are more or less comparable to those obtained by using tetrabutylammonium fluoride. However, the both method provides final product e.g. paclitaxel or docetaxel, which are comparatively easier to purify to pharmaceutical grade material.

The free amines 8 are treated with acid chlorides or acid anhydrides in the presence of a base in a heterogeneous phase to obtain intermediates 9.

The intermediate 9, under mild alkaline condition, in the presence of ammonia or aliphatic amines or aromatic amines or their combination, preferably ammonia and pyridine (1:10) undergoes selective deprotection of 2-haloacyl groups without any appreciable degradation. The reaction is carried out at 0–5° C., preferably 2° C. under stirring for 6–24 h, preferably 10 h to obtain paclitaxel or docetaxel. (4S,5R)-4-Phenyl-2-substituted-3-[(2-unsubstituted/substituted-2-trialkylsilyl)ethoxycarbonyl]-1,3-oxazolidine-5-carboxylic acids 1 is synthesised as described below.

i) a condensation of a haloformate such as a (2-unsubstituted/substituted-2-trialkylsilyl)ethyl haloformate with arylisoserine 2 e.g. phenylisoserine in the presence of a base such as alkali hydroxide or carbonate or bicarbonate or any other acid neutralizing chemical.

ii) the isoserine 3 thus obtained, is then converted into the corresponding ester 4 in the presence of an alcohol, preferably methanol and an activating agent such as dicyclohexylcarbodiimide or carbonyldiimidazole. The methyl ester 4 is alternatively prepared by condensing the intermediate 3 with diazomethane or treating it with alkyl halide in the presence of a base such as potassium bicarbonate in acetone.

iii) the isoserine ester 4 is then converted into 3-[(2-unsubstituted/substituted-2-trialkylsilyl)ethoxycarbonyl]-5-oxazolidine carboxylic ester 5 in the presence of chemicals such as alkoxyalkane or gem-dialkoxyalkane or 1,1,1-trialkoxyalkane. The reaction is catalyzed by p-arylsulfonic acid or their pyridinium salt.

iv) 5-oxazolidine carboxylic ester 5 is finally converted into the corresponding acid 1 by hydrolysis with alkali hydroxide or carbonate followed by treatment with a mineral acid.

EXPERIMENTAL

Synthesis of 7-O-chloroacetylbaccatin III (6a)

A mixture of 10-deacetylbaccatin III (250 gm, 0.46 mole), pyridine (150 gm) and 4-DMAP (5.6 gm, 46 mmol) is dissolved in dichloromethane (2.0 L). The reaction mixture is stirred for 10 minutes. Chloro acetylchloride (75 gm, 0.66 mole) dissolved in dichloromethane (1.5 L) is then slowly added to the reaction mixture at 25–30° C. The whole mixture is stirred for 20 minutes and then excess reagent is decomposed by adding 100 gm ice water, and acidified with 5% hydrochloric acid. The organic layer thus obtained is successively washed with aqueous sodium bicarbonate, sodium chloride solution, dried over anhydrous sodium sulfate, and then distilled under reduced pressure. The residue is dissolved in toluene (1.5 L) at 70–80° C. and then cooled down to 0–5° C. The resulting fine solid is filtered and then washed with 1000 ml of hexane to obtain the pure title compound 6a (250 gm, 0.40 mole, yield 87%).

Synthesis of 7-O-chloroacetylbaccatin III (6c)

7-O-Chloroacetyl-10-deacetylbaccatin III 6a(250 gm, 0.40 mole) is dissolved in pyridine (2.5 L). The reaction mixture is cooled to 0–5° C. 190 gm (2.42 mole) of acetyl chloride is slowly added to the reaction mixture at 0–5° C. over a period of 40–50 min. Then the resulting mixture is further stirred at 0–5° C. for 3 h. The excess reagent is decomposed by adding 200 ml water maintaining internal temperature 0–5° C. The solvent is then removed under reduced pressure and the residual mass is extracted with 2.5 L of ethyl acetate. The organic layer thus obtained is washed with aqueous hydrochloric acid, sodium bicarbonate and sodium chloride solution. The organic layer is evaporated under reduced pressure. The residue is dissolved in toluene (1.5 L) at 70–80° C. and then cooled down to 0° C. The resulting fine solid is filtered and then washed with 800 ml of hexane to obtain the pure title compound 6c (249.1 gm, 0.376 mole, yield 94%).

Synthesis of 7,10-di-O-chloroacetyl-10-deacetylbaccatin III (6b)

A mixture of 10-deacetylbaccatin III (250 gm, 0.46 mole), pyridine (300 gm) and 4-DMAP (11.2 gm, 92 mmol) is dissolved in 2.0 L of dichloromethane. The reaction mixture is stirred for 10 minutes. 150 gm (1.33 mole) of chloroacetyl chloride dissolved in 1.5 L dichloromethane is slowly added to the reaction mixture at 25–30° C. Then, the whole mixture is stirred for 20 minutes. 150 gm ice water is added to decompose the excess reagent, and then the reaction mixture is acidified with 5% hydrochloric acid. The organic layer thus obtained is successively washed with aqueous sodiumbicarbonate, sodium chloride solution, dried over anhydrous sodium sulfate, and then distilled under reduced pressure. The residue is dissolved in toluene (1.5 L) at 70–80° C. and then cooled down to 0–5° C. The resulting fine solid is filtered and then washed with 1000 ml of hexane to obtain the pure title compound 6b (304.6 gm, 0.437 mole, yield 95%).

7-O-[2-(Chloroacetyl)]-13-[(4S,5R)-2-p-methoxyphenyl-4-phenyl-3-(2-phenyl-2-trimethylsilyl)ethoxycarbonyl]-1,3-oxazolidinyl-5-carbonyl]baccatin III (7a)

A mixture of 7-O-(2-chloroacetyl)baccatin III (6c, 100 gm, 0.15 mole), (4S,5R)-2-p-methoxyphenyl-3-[(2-phenyl-2-trimethylsilyl)ethoxycarbonyl]-4-phenyl-1,3-oxazolidine-5-carboxylic acid (1a, 83 gm, 0.16 mole) and 4-dimethylaminopyridine (5.0 gm, 40.9 mmol) is dissolved in toluene (0.8 L) under nitrogen atmosphere. The temperature of the reaction mixture is raised to 50° C. under stirring and then a solution of DCC (45 gm, 0.22 mole) in toluene (0.2 L) is added to it. Exotherm occurs and the temperature of the reaction mixture automatically rises to 60° C. and that temperature is maintained for 30 minutes. The reaction mixture is then cooled to 25–30° C., diluted with ethyl acetate (2.5 L) and kept under stirring for 15 minutes. The reaction mixture is then filtered under suction. The residue is extracted with ethyl acetate (2×1.0 L). The combined organic layer is washed successively with 25% ammonium chloride solution, 5% aqueous sodium bicarbonate, water, and brine and then dried over anhydrous sodium sulfate. Evaporation of the organic layer under reduced pressure affords the crude product, which is then precipitated with DCM/Hexane (1:10) to obtain compound 7a (164 gm, 0.14 mole, 93.3%).

7,10-Di-O-[2-chloroacetyl]-13-[(4S,5R)-2-p-methoxyphenyl-4-phenyl-3-(2-phenyl-2-trimethylsilyl)ethoxycarbonyl]-1,3-oxazolidinyl-5-carbonyl]-10-deacetylbaccatin III (7b)

The compound 7b is obtained from 7,10-di-O-(2-chloroacetyl)-10-deacetylbaccatin III (6b, 110 gm, 0.158 mole), (4S,5R)-2-p-methoxyphenyl-3-[(2-phenyl-2-trimethylsilyl) ethoxycarbonyl]-4-phenyl-1,3-oxazolidine-5-carboxylic acid (1a, 88.6 gm, 0.17 mole) and 4-dimethylaminopyridine (5.27 gm, 43.1 mmol) and DCC (47.8 gm, 0.23 mole) in toluene (1.1 L) by following the protocol described above for the compound 7a.

Yield: 178 gm, 0.148 mole, 94%).

7-O-[2-chloroacetyl]-13-[(4S,5R)-2-p-methoxyphenyl-4-phenyl-3-(2-trimethylsilyl)ethoxy-carbonyl]-1,3-oxazolidinyl-5-carbonyl] baccatin III (7c)

The compound 7c is obtained from 7-O-(2-chloroacetyl) baccatin III (6c, 100 gm, 0.15 mole), (4S,5R)-2-p-methoxyphenyl-4-phenyl-3-[(2-trimethylsilyl)ethoxycarbonyl]-1,3-oxazolidine-5-carboxylic acid (1b, 71 gm, 0.16 mole) and 4-dimethylaminopyridine (5.0 gm, 40.93 mole) and DCC (45 gm, 0.22 mole) in toluene (1.0 L) by following the protocol described above for the compound 7a.

Yield: 155 gm, 0.14 mole, 94.4%

7,10-Di-O-[2-(Chloroacetyl)]-13-[(4S,5R)-2-p-methoxyphenyl-4-phenyl-3-(2-trimethylsilyl)-ethoxycarbonyl]-5-oxazolidinyl carbonyl]-10-decaetylbaccatin III (7d)

The compound 7d is obtained from 7,10-di-O-(2-chloroacetyl)-10-deacetylbaccatin III (6b, 100 gm, 0.14 mole), (4S,5R)-2-p-methoxyphenyl-4-phenyl-3-[(2-trimethylsilyl) ethoxycarbonyl]-1,3-oxazolidine-5-carboxylic acid (1b, 66.2 gm, 0.149 mole) and 4-dimethylaminopyridine (4.67 gm, 38.2 mmol) and DCC (42.4 gm, 0.205 mole) in toluene (1.0 L) by following the protocol described above for the compound 7a.

Yield: 149.5 gm, 0.133 mole, 95%

7-O-12-chloroacetyl]-13-[(4S,5R)-2,2'-dimethyl-4-phenyl-3-[2-(trimethylsilyl) ethoxycarbonyl]-1,3-oxazolidinyl-5-carbonyl]baccatin III (7e)

The compound 7e is obtained from 7-O-(2-chloroacetyl) baccatin III (6c, 100 gm, 0.15 mole), (4S,5R)-2,2-dimethyl-]-4-phenyl-3-[(2-trimethylsilyl)ethoxycarbonyl-1,3-oxazolidine-5-carboxylic acid (1c, 58.5 gm, 0.16 mole) and 4-dimethylaminopyridine (5.0 gm, 40.93 mmol) and DCC (45 gm, 0.22 mole) in toluene (1.0 L) by following the protocol described above for the compound 7a.

Yield: 144 gm, 0.14 mole, 94.5%.

7,10-O-[2-chloroacetyl]Dichloroacetyl-13-[(4S,5R)-2,2'-dimethyl-4-phenyl-3-[2(trimethylsilyl) ethoxyarbonyl]-1,3-oxazolidinyl-5-carbonyl]-10-baccatin III (7f)

The compound 7f is obtained from 7,10-O-di-(2-chloroacetyl)baccatin III (6b, 100 gm, 0.14 mole), (4S,5R)-2,2-dimethyl-]-4-phenyl-3-[(2-trimethylsilyl)ethoxycarbonyl-1,3-oxazolidine-5-carboxylic acid (1c, 54.8 gm, 0.15 mole) and 4-dimethylaminopyridine (4.68 gm, 38.3 mmol) and DCC (42.4 gm, 0.205 mole) in toluene (1.0 L) by following the protocol described above for the compound 7a.

Yield: 136 gm, 0.13 mole, 92.8%.

7-O-(2-Chloroacetyl)paclitaxel (9a)

7-O-[2-(Chloroacetyl)]-13-[(4S,5R)-2-p-methoxyphenyl-4-phenyl-3-(2-phenyl-2-trimethylsilyl)-ethoxycarbonyl]-1,3-oxazolidinyl-5-carbonyl] baccatin III (7a, 116.4 gm, 0.1 mole) is suspended in dichloromethane (1.17 L) at 25–30° C. To the stirred solution is added 2 equivalents of tetrabutylammonium fluoride trihydrate (63.1 gm, 0.2 mole). Stirring is continued for 30 minutes at 25° C. and then 5% aqueous sodium bicarbonate (11.8 gm, 0.14 mole, 236 ml) is added. The reaction mixture is cooled to 0–5° C. and then a solution of benzoyl chloride (17.4 ml, 0.149 mole) in dichloromethane (350 ml) is added at the same temperature over a period of 20 minutes. After the addition is over, stirring is continued for 15 minutes. The organic layer is separated, washed with brine, and dried over anhydrous sodium sulfate. The solvent is evaporated under reduced pressure and the residue is subjected to column chromatography (eluent: ethylacetate/hexane, 2/5, v/v) to obtain the title compound 9a (77 gm, 0.083 mole, 83%).

Alternative method: 7-O-[2-(Chloroacetyl)]-13-[(4S,5R)-2-p-methoxyphenyl-4-phenyl-3-(2-trimethylsilyl)ethoxycarbonyl]-1,3-oxazolidinyl-5-carbonyl]baccatin III (7c, 110 gm, 0.1 mole) is suspended in 60% aqueous trifluoroacetic acid (1.1 L, 10 times) and then stirred at 18–22° C. for 4.5 h, when TLC indicates completion of the reaction. The reaction mixture is then diluted with dichloromethane and poured into a solution of sodium hydrogen phosphate (2.5 Kg) in water (5.0 L) under stirring. The organic layer is cooled to 0–5° C. and then a precooled solution of 5% aqueous sodium bicarbonate (11.8 gm, 0.14 mole, 236 ml) is added under stirring. A solution of benzoyl chloride (17.4 ml, 0.149 mole) in dichloromethane (350 ml) is added slowly over a period of 20 minutes to the above reaction mixture at the same temperature. After the addition is over, stirring is continued for 15 minutes. The organic layer is then separated, washed with brine, and dried over anhydrous sodium sulfate. The solvent is evaporated under reduced pressure and the residue is subjected to column chromatography (eluent: ethyl acetate/hexane, 2/5, v/v) to obtain the title compound 9a (74.5 gm, 0.08 mole, 80%)

Alternative method: 7-Chloroacetyl-13-[(4S,5R)-2,2'-dimethyl-4-phenyl-3-[2-(trimethylsilyl)ethoxyarbonyl]-1,3-oxazolidinyl-5-carbonyl]baccatin III (7e, 101 gm, 0.1 mole) is dissolved in 1.0L of 60% aqueous TFA-water and the mixture is stirred at 18–22° C. temperature for 4 h. After completion of reaction the reaction mixture is diluted with dichloromethane (2.0 L) and then poured into a solution of disodium hydrogen phosphate (2.5 Kg) in water (5.0) under stirring. The dichloromethane layer is separated and sodium bicarbonate (11.8 g 0.14 mole in 236 ml of water) was added to the mixture, cooled to 0–2° C. and then benzoyl chloride (17.4 ml, 0.149 mole) dissolved in dichloromethane (350 ml) is added dropwise thereto. After addition the reaction mixture is stirred at 28–32° C. for 2 h. The organic layer is separated and washed with brine and then dried over anhydrous sodium sulfate. The solvent is evaporated under reduced pressure and the residue is subjected to column chromatography (eluent: ethylacetate/hexane, 2/5, v/v) to obtain the title compound 9a (75.0 gm, 0.08 mole, 80%) as a white solid.

7,10-Di-O-(2-chloroacetyl)docetaxel (9b)

7,10-Di-O-[2-(Chloroacetyl)]-13-[(4S,5R)-2-p-methoxyphenyl-4-phenyl-3-(2-phenyl-2-trimethyl-silyl)ethoxycarbonyl]-1,3-oxazolidinyl-5-carbonyl]-10-deacetylbaccatin III (7b, 120 gm, 0.1 mole) is suspended in dichloromethane (1.2 L) at 25–30° C. To the stirred reaction mixture is added 4 equivalents of tetrabutylammonium fluoride trihydrate (126.21 gm, 0.4 mole). Stirring is continued for 30 minutes at 25° C. and the reaction is monitored by TLC. After the reaction is over dichloromethane is evaporated under reduced pressure. The residue is taken in toluene (2.0 L) and stirred at 25–30° C. To the stirred solution is added sodium bicarbonate (11.8 gm), followed by di-tertbutyl dicarbonate (30.55 gm, 0.14 mole) under stirring. The reaction mixture is stirred for further 3 h and then sodium bicarbonate is removed by filtration. The organic layer is evaporated under reduced pressure at 35–40° C. The residue is taken in ethyl acetate (2.4 L), washed with brine and dried over anhydrous sodium sulfate. Evaporation of the organic layer under reduced pressure affords the compound 9b (78.8 gm, 0.082 mole, 82%).

Alternative Procedure: 7,10-Di-O-[2-(chloroacetyl)]-13-[(4S,5R)-2-p-methoxyphenyl-4-phenyl-3-(2-trimethylsilyl)ethoxycarbonyl]-5-oxazolidinyl carbonyl]-10-deacetylbaccatin III (7d, 105 gm, 0.1 mole) is suspended in 60% aqueous trifluoroacetic acid (1.05 L, 10 times) and then stirred at 18–22° C. for 4.5 h, when TLC indicates completion of the reaction. The reaction mixture is then diluted with dichloromethane (2.0 L) and poured into a solution of disodium hydrogen phosphate (2.5 Kg) in water (5.0 L). The organic layer is separated, washed with water, brine and dried over anhydrous sodium sulfate. Evaporation of the organic layer affords the corresponding free amine 8b. which is then converted to compound 9b (75 gm, 0.07 mole, 80%).

Alternative Procedure: 7,10-Di-O-[2-chloroacetyl]-13-[(4S,5R)-2,2-dimethyl-4-phenyl-3-(2-trimethylsilyl)ethoxycarbonyl]-5-oxazolidinyl carbonyl]-10-deacetylbaccatin III (7f, 112 gm, 0.099 mole) is suspended in 60% aqueous trifluoroacetic acid (1.12 L, 10 times) and then stirred at 18–22° C. for 4.5 h, when TLC indicates completion of the reaction. The reaction mixture is then diluted with dichloromethane (2.0 L) and poured into a solution of sodium hydrogen phosphate (2.5 Kg) in water (5.0 L). The organic layer is separated, washed with water, brine and dried over anhydrous sodium sulfate. Evaporation of the organic layer affords the corresponding free amine 8b. The latter is taken in tetrahydrofuran (2.0 L) and then sodium bicarbonate (11.6 gm, 0.138 mole) followed by di-tert-butyl dicarbonate (30.55 gm, 0.14 mole) is added under stirring. After the addition is over, stirring is continued for 3 h and then sodium bicarbonate is removed by filtration. The organic layer is evaporated under reduced pressure at 35–40° C. The residue is taken in ethyl acetate (2.5 L), washed with brine and dried over anhydrous sodium sulfate. Evaporation of the organic layer under reduced pressure affords the compound 9b (76 gm, 0.079 mole, 79%).

Paclitaxel (10a)

To a precooled solution (0–5° C.) of 25% ammonia (150 ml) in pyridine (750 ml) is added 7-O-(2-chloroacetyl) paclitaxel (9a, 75 gm, 80.6 mmol) and then stirred at this temperature for 12 h. The reaction is monitored by TLC. After the reaction is over, ammonia and pyridine is removed under low pressure. The resultant gum is dissolved in ethyl acetate (1.5 L). The organic layer is washed successively with 2% hydrochloric acid, 5% sodium bicarbonate solution, and brine and then stored over anhydrous sodium sulfate. Evaporation of the organic layer under reduced pressure affords crude paclitaxel. The latter is on column chromatography on silica 60 with ethyl acetate/hexane (6/4) affords paclitaxel (57.8 gm, 67.69 mmol, 84%) as a white solid.

Docetaxel (10b)

Docetaxel is obtained from 7,10-di-O-(2-chloroacetyl) docetaxel (9b, 75 gm, 0.078 mole) using 25% ammonia (300 ml) in pyridine (1500 ml) and by following the protocol described above for paclitaxel. After column chromatography on silica 60 with ethyl acetate/hexane (6/4) docetaxel is obtained as a white solid. Yield: 50.5 gm, 0.0625 mole, 80.1%.

We claim:

1. A process for preparation of taxanes of formula 10:

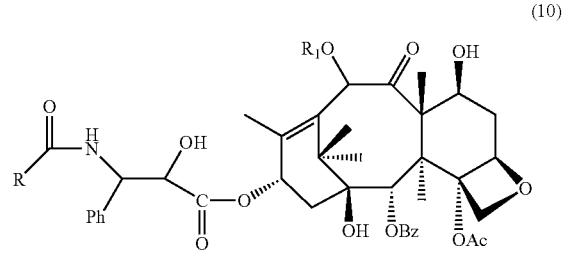

(10)

wherein R is phenyl or tertiary butoxy and $R_1$ is hydrogen, acetyl or chloroacetyl, wherein the process comprises the steps of:
i) reacting compound of formula 6, wherein R1 is hydrogen, acetyl or chloroacetyl

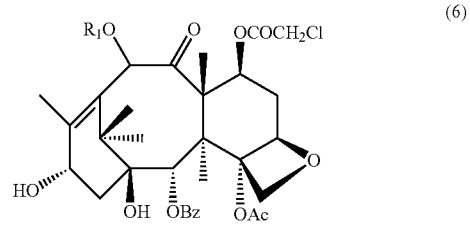

(6)

with (4S,5R)-3-[(2'-substituted or unsubstituted-2'-trialkylsilyl) ethoxy-carbonyl]-4-phenyl-2-mono or di-substituted-1,3-oxazolidine-5-carboxylic acid of formula 1,

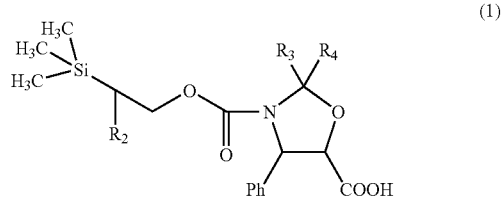

(1)

wherein $R_2$ is hydrogen or phenyl, $R_3$ is alkyl ($C_1$ to $C_4$) or p-methoxy phenyl and $R_4$ is hydrogen or alkyl ($C_1$ to $C_4$) in the presence of 4-dimethylaminopyridine, dicyclohexylcarbodiimide (DCC) and an aromatic hydrocarbon solvent to give compound of formula 7,

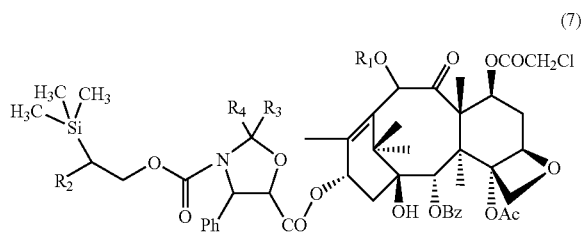

(7)

wherein $R_1$ is hydrogen, acetyl or chloroacetyl, $R_2$ is hydrogen or phenyl, $R_3$ is alkyl ($C_1$ to $C_4$) or p-methoxy phenyl and $R_4$ is hydrogen or alkyl ($C_1$ to $C_4$);

ii) reacting compound of formula 7 with a tetra alkyl ammonium halide in the presence of a haloalkane solvent to give compound of formula 8,

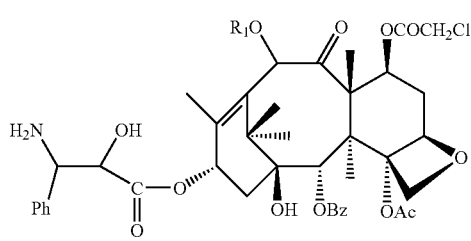

(8)

wherein $R_1$ is hydrogen, acetyl or chloroacetyl;

iii) reacting the solution of compound of formula 8 in the haloalkane solvent with an acid chloride or acid anhydride in the presence of an aqueous solution of a base to give compound of formula 9,

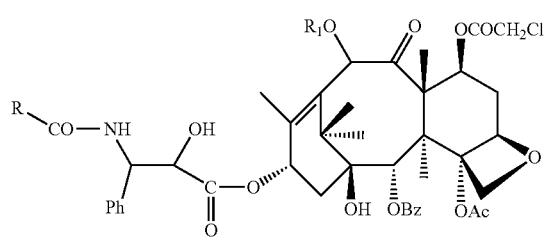

(9)

wherein R is phenyl or tertiary butoxy and $R_1$ is hydrogen; acetyl or chloroacetyl; and iv) treating the compound of formula 9 with aqueous ammonia in the presence of pyridine at a temperature of between −20° to +40° C. to give taxane compound of formula 10.

2. A process as claimed is claim 1, wherein the aromatic hydrocarbon solvent is toluene.

3. A process as claimed in claim 1, wherein step-i) is carried out at a temperature of between 0–100° C.

4. A process as claimed in claim 1, wherein the tetraalkylammonium halide is tetrabutyl ammonium fluoride.

5. A process as claimed in claim 1, wherein the haloalkane solvent is dichloromethane.

6. A process as claimed in claim 1, wherein, the ratio of aqueous ammonia and pyridine is 1:10 weight by weight.

7. A compound of formula 8,

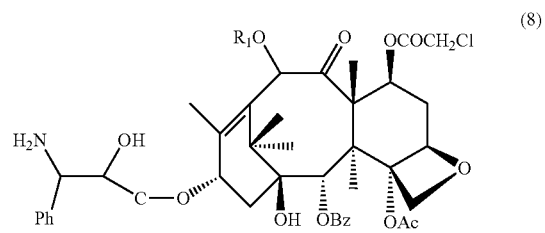

(8)

wherein $R_1$ is acetyl or chloroacetyl.

8. A compound of formula 9

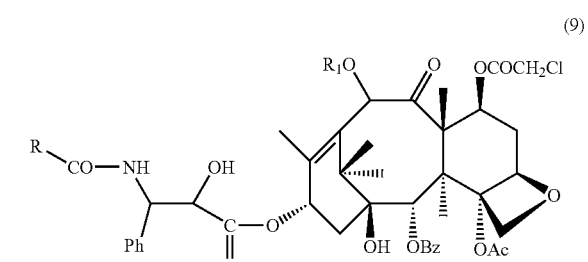

(9)

wherein R is phenyl or tertiary butoxy and $R_1$ is acetyl or chloroacetyl.

9. A compound of formula 8:

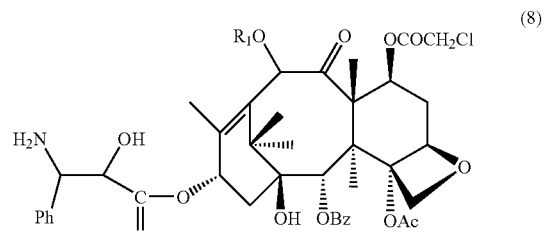

(8)

wherein $R_1$ is hydrogen, acetyl or chloroacetyl.

* * * * *